United States Patent [19]

Ozaki et al.

[11] Patent Number: 4,908,312

[45] Date of Patent: Mar. 13, 1990

[54] PROCESS FOR PRODUCING PHENYLANANINE

[75] Inventors: Akio Ozaki; Ryoichi Katsumata, both of Machida; Tetsuo Oka, Yokohama, all of Japan

[73] Assignee: Kyowa Hakko Kogyo Co., Ltd., Tokyo, Japan

[21] Appl. No.: 281,920

[22] Filed: Dec. 7, 1988

Related U.S. Application Data

[63] Continuation of Ser. No. 613,209, May 23, 1984, abandoned.

[30] Foreign Application Priority Data

May 28, 1983 [JP] Japan .................................. 58-94392

[51] Int. Cl.$^4$ ..................... C07H 21/00; C12N 15/00; C12N 1/20; C12P 13/22; C12R 1/13; C12R 1/15
[52] U.S. Cl. ............................. 435/108; 435/252.32; 435/840; 435/843; 935/29; 935/60; 935/72; 536/27
[58] Field of Search .................. 435/108, 172.3, 252.32, 435/320, 840, 843; 935/14, 27, 29, 72; 536/27

[56] References Cited

U.S. PATENT DOCUMENTS

| | | | |
|---|---|---|---|
| 3,660,235 | 5/1972 | Okumura et al. | 435/108 |
| 4,407,952 | 10/1983 | Tsuchida et al. | 435/108 |
| 4,495,283 | 1/1985 | Araki | 435/107 |
| 4,500,640 | 2/1985 | Katsumata et al. | 435/253 |
| 4,514,502 | 4/1985 | Miwa et al. | 435/172.3 X |
| 4,560,654 | 12/1985 | Miwa et al. | 435/115 |
| 4,591,562 | 5/1986 | Kurahashi et al. | 435/108 |
| 4,601,983 | 7/1986 | Nakamori et al. | 435/172.3 X |

FOREIGN PATENT DOCUMENTS

| | | | |
|---|---|---|---|
| 0553843 | 5/1986 | Australia | 435/172.3 |
| 0066129 | 12/1982 | European Pat. Off. | 435/172.3 |
| 0071023 | 2/1983 | European Pat. Off. | 435/172.3 |
| 0082485 | 6/1983 | European Pat. Off. | 435/317 |
| 0088166 | 9/1983 | European Pat. Off. | 435/172.3 |
| 0093611 | 11/1983 | European Pat. Off. | 435/317 |
| 0131171 | 1/1985 | European Pat. Off. | 435/172.3 |
| 2076853 | 12/1981 | United Kingdom | 435/172.3 |

OTHER PUBLICATIONS

Gowrishankar, J. et al., *J. Bacteriol.*, pl vol. 150, No. 3, pp. 1130–1137, 1982.

Zurawski, G. et al., *Proc. Natl. Acad. Sci.*, vol. 75, No. 10, pp. 4271–4275, 1978.

Fazel, A. et al., *Archnes Biochem. and Biophys.*, vol. 200, No. 1, pp. 165–176, 1980.

Ozaki A. et al., *Agric. Biol. Chem.*, vol. 49(10), pp. 2925–2930, 1985.

Follettie, M. et al. *J. Bacteriol.*, vol. 167, No. 2, pp. 695–702, 1986.

Ozaki et al., "Functional Expression of the Genes of *E. coli* in Gram—Positive *Corynebacterium Glutamicum*", *Mol Gen Genet*, 196:175–178, 1984.

Goiorishankar, J., et al., "Molecular Cloning of phe R in E. coli K12", *Journal of Bacteriology*, 152(1): 1–6, 1982.

Schmid, *J. Bact.*, vol. 151, No. 1, (1982), 68:76.

Primary Examiner—Jayme A. Huleatt
Attorney, Agent, or Firm—Fitzpatrick, Cella, Harper & Scinto

[57] ABSTRACT

The invention relates to a bacterial process for producing phenylalanine. The process utilizes a Corynebacterium or Brevibacterium host which is transformed with a recombinant DNA. The recombinant DNA harbors a DNA containing a gene which encodes chorismate mutase or prephenate dehydratase. The transformed microorganism is then cultured in order to accumulate phenylalanine in the culture medium and the phenylalanine is recovered therefrom.

5 Claims, No Drawings

PROCESS FOR PRODUCING PHENYLANANINE

This application is a continuation of application Ser. No 613,209, filed May 23, 1984, now abandoned.

BACKGROUND OF THE INVENTION

For the direct production of phenylalanine by fermentation methods using mutant strains resistant to phenylalanine analog of the bacteria belonging to the genus *Corynebacterium, Brevibacterium*, and the like are known.

No example of expressing a desired gene in a host microorganism belonging to the genus *Corynebacterium* or *Brevibacterium* by introducing a recombinant DNA containing such desired gene and vector, one of which is foreign to a host microorganism, into such host microorganism has been reported. In the recombinant DNA technology using a microorganism belonging to the genus *Corynebacterium* or *Brevibacterium* as a host, it is necessary to construct vectors autonomously replicable in these microorganisms, having selectable markers and useful for cloning of desired genes, and to establish an efficient transformation system. Furthermore, methods to overcome various barriers against the expression of foreign recombinant DNA will be necessary.

The present inventors have constructed plasmid vectors autonomously replicable in a microorganism belonging to the genus *Corynebacterium* or *Brevibacterium* and having selectable markers and adequate cloning sites and have developed a highly efficient transformation system (Japanese Published Unexamined Patent Application Nos. 183799/82, 186492/82 and 186489/82). Further, the present inventors have found that the plasmid vectors are useful for expressing a foreign gene in a host microorganism and increasing the productivity of amino acids by ligating a DNA fragment containing a foreign gene involved in the biosynthesis of amino acids such as glutamic acid and lysine to the plasmid vectors according to the procedures in recombinant DNA technology (U.S. Pat. No. 4,237,224 and Methods in Enzymology 68, Recombinant DNA, edited by Ray Wu, Academic Press 1979) and transforming *Corynebacterium glutamicum* L-22 or its derivatives using the transformation methods described in Japanese Published Unexamined Patent Application No. 126789/83.

Furthermore, the present inventors have found that a microorganism prepared by the same method has acquired an increased productivity of phenylalanine.

SUMMARY OF THE INVENTION

This invention relates to a process for producing phenylalanine by a novel expression method of a gene. More specifically, the present invention is a process for producing phenylalanine by transforming a host microorganism belonging to the genus *Corynebacterium* or *Brevibacterium* with a recombinant DNA of a DNA fragment containing a gene involved in the biosynthesis of phenylalanine and a vector DNA, culturing the transformant in a nutrient medium, accumulating phenylalanine in the culture medium and recovering phenylalanine therefrom.

DESCRIPTION OF THE INVENTION

The present invention provides a process for producing phenylalahine by culturing in a medium a transformant which is obtained by transforming a microorganism belonging to the genus *Corynebacterium* or *Brevibacterium* with a recombinant DNA of a DNA fragment containing a gene involved in the biosynthesis of phenylalanine and a vector DNA.

As the DNA fragment containing the gene used in the present invention, the DNA fragment containing a gene involved in the biosynthesis of phenylalanine derived from prokaryotes is used. As the gene derived from prokaryotes, the gene derived from a bacterium belonging to the genus *Escherichia, Corynebacterium, Brevibacterium, Bacillus, Staphylococcus* or *Serratia* and responsible for the biosynthesis of phenylalanine or the metabolism relating to the biosynthesis is preferably used.

As the gene responsible for the biosynthesis of phenylalanine or the metabolism relating to the biosynthesis, the gene encoding for chorismate mutase and/or prephenate dehydratase is used. Further, a gene additionally containing a gene responsible for the resistance to phenylalanine, tyrosine or an analog thereof such as parafluorophenylalanine (PFP) is used.

For example, the chromosomal DNA of *Corynebacterium glutamicum* K38 (resistant to PFP) is used as a source of the desired gene.

The vector used in the present invention should autonomously replicate in cells of the host microorganism. Preferably, plasmids isolated from microorganisms belonging to the genus *Corynebacterium* by the present inventors or derivatives thereof such as pCG1 (Japanese Published Unexamined patent application No. 134500/82), pCG2 (Japanese Published Unexamined patent application No. 35197/83), pCG4 (Japanese Published Unexamined patent application No. 183799/82), pCE53, pCE54, pCG11 and pCB101 are used.

Microorganisms carrying the following plasmids have been deposited with the Fermentation Research Institute, Agency of Industrial Science and Technology, Ibaraki, Japan and the American Type Culture Collection, Rockville, Md., U.S.A. under the following accession numbers.

| Plasmid | FERM P- | ATCC |
|---------|---------|-------|
| pCG1    | 5865    | 31808 |
| pCG2    | 5954    | 31832 |
| pCG4    | 5939    | 31830 |
| pCE54   | —       | 39019 |
| pCG11   | —       | 39022 |
| pCB101  | —       | 39020 |

Of the foregoing plasmids, pCG11 is most preferred.

Plasmid pCG11 is a plasmid constructed by the present inventors and described in Japanese Published Unexamined patent application No. 134500/82 and U.S. patent application Ser. No. 346,867. Plasmid pCG11 is prepared by inserting the BamHI fragment containing a gene responsible for resistance to streptomycin and/or spectinomycin (referred to as $Sm^R/Spec^R$ gene hereinafter) of plasmid pCG4 isolated from *Corynebacterium glutamicum* 225-250 (ATCC 31830, FERM P-5939) into the unique BglII cleavage site of plasmid pCG1 isolated from *Corynebacterium glutamicum* 225-57 (ATCC 31808, FERM P-5865) using the same cohesive ends of both fragments.

Plasmid pCG11 has a molecular weight of about 6.8 Kb and a single cleavage site for BglII and PstI and gives $Sm^R/Spec^R$ phenotype.

Transformation with the ligated DNA mixture is carried out using protoplasts of the genus *Corynebacterium*. or *Brevibacterium*, and the method described in U.S. patent application Ser. No. 368,034, filed April 13, 1982 and Japanese Published Unexamined Patent Application Nos. 186492/82 and 186489/82. Streptomycin or spectinomycin is used for selection. Transformants are recovered as a colony regenerated on a hypertonic agar medium containing 100–400 µg/ml streptomycin or 200–1000 µg/ml spectinomycin which does not allow the reversion to normal cells of protoplast which are not treated with the ligation mixture. Alternatively, transformants are regenerated unselectively on a regeneration medium, and the resultant cells are scraped and resuspended, followed by the isolation of those cells grown on an agar medium containing a drug in a concentration wherein the recipient normal cells cannot grow, that is, generally 5–50 µg/ml streptomycin, 50–500 µg/ml spectinomycin.

Plasmid DNAs in the transformants can be isolated from cultured cells of the transformants and purified according to the methods described in U.S. patent application Ser. No. 346,867 filed Feb. 8, 1982 and Japanese Published Unexamined patent application Nos. 134500/82 and 186489/82. The structures of the DNAs can be determined by digesting them with various restriction endonucleases and analyzing the DNA fragments by agarose gel electrophoresis. The plasmid isolated from one of the transformants is named pCG11.

Recovery of plasmids from the strains is carried out according to the methods described in U.S. patent applications, Ser. No. 346,867, filed Feb. 8, 1982, Ser. No. 368,035 filed April 13, 1982 and Ser. No. 410,887 filed Aug. 24, 1982 and Japanese Published Unexamined patent application Nos. 134500/82 and 183799/82 and 35197/83.

Preparation of a recombinant DNA of a vector DNA with a DNA fragment containing a gene is carried out by conventional in vitro recombinant DNA technology, e.g. cleavage and ligation of a donor DNA containing a desired gene to a vector DNA (refer to Japanese Published Unexamined Patent Application No. 126789/83, USP 4,237,224).

The ligase reaction gives recombinants containing genes other than the desired gene. The desired recombinant DNA can be obtained by directly transforming a microorganism of the genus *Corynebacterium* or *Brevibacterium* with the DNA mixture, selecting the transformants having the phenotype derived from the desired gene and isolating the desired recombinant DNA from the cultured cells of the transformants. Instead of cloning the desired gene directly in a microorganism of the genus *Corynebacterium* or *Brevibacterium*, the desired gene can be cloned by using another host-vector system such as *Escherichia coli*. Then, it is recloned in vitro into a vector of the genus *Corynebacterium* or *Brevibacterium* to transform these microorganisms and transformants containing the desired recombinant plasmid are selected as mentioned above.

The following references are helpful for the construction of recombinant DNA:

S.N. Cohen, et al., U.S.P. No. 4,237,224;
Idenshi Sosa Jikkenho, edited by Yasuyuki Takagi, printed by Kodansha Scientific (1980);
Methods in Enzymology 68, Recombinant DNA edited by Ray Wu, Academic Press, 1979
Japanese Published Unexamined patent application No. 126789/83

Microorganisms belonging to the genus *Corynebacterium* or *Brevibacterium* and which are competent for incorporating DNAs may be used as the host microorganisms in the present invention. The following are examples of a suitable host microorganism.

|  | Accession Number | |
| --- | --- | --- |
|  | FERM P- | ATCC |
| *Corynebacterium glutamicum* L-15 | 5946 | 31834 |
| *Corynebacterium glutamicum* K-38 | 7087 |  |
| *Corynebacterium herculis* |  | 13868 |
| *Corynebacterium herculis* L-103 | 5947 | 31866 |
| *Brevibacterium divaricatum* L-204 | 5948 | 31867 |
| *Brevibacterium lactofermentum* |  | 13869 |
| *Brevibacterium lactofermentum* L-312 | 5949 | 31868 |
| *Brevibacterium flavum* |  | 14067 |

Transformation of the host microorganisms with recombinant DNAs is carried out by the following steps:

(1) Preparation of protoplasts of host cells;
(2) Transformation of the protoplasts with a recombinant DNA;
(3) Regeneration of the protoplasts to normal cells and selection of a transformant;

These steps are described in detail below.

1. Preparation of protoplasts of host cells:

The preparation of protoplasts is carried out by culturing a microorganism under conditions which render it sensitive to lysozyme, a lytic enzyme, and treating the cultured cells with lysozyme in a hypertonic solution to remove the cell walls. In order to render microbial cells sensitive to lysozyme, reagents inhibiting the synthesis of bacterial cell walls are used. For example, microbial cells sensitive to lysozyme are obtained by adding, during the logarithmic growth phase, an amount of penicillin which does not inhibit or sub-inhibits the growth and then continuing culturing for several generations.

For culturing, any medium wherein the microorganism can grow may be used. For example, a nutrient medium NB (pH 7.2) consisting of 20 g/l powdered bouillon and 5 g/l yeast extract and a semi-synthetic medium SSM (pH 7.2) consisting of 10 g/l glucose, 4 g/l NH$_4$Cl, 2 g/l urea, 1 g/l yeast extract, 1 g/l KH$_2$PO$_4$, 3 g/l K$_2$HPO$_4$, 0.4 g/l MgCl$_2$.6H$_2$O, 10 mg/l FeSO$_4$.7H$_2$O, 0.2 mg/l MnSO$_4$. (4–6)H$_2$O, 0.9 mg/l ZnSO$_4$.7H$_2$O, 0.4 mg/l CuSO$_4$.5H$_2$O, 0.09 mg/l Na$_2$B$_4$O$_7$.10H$_2$O, 0.04 mg/l (NH$_4$)$_6$Mo$_7$O$_{24}$4H$_2$O, 30 µg biotin and 1 mg/l thiamine hydrochloride are used. Microbial cells are inoculated in the medium and culturing is carried out with shaking. The optical density (OD) of the culture medium at 660 nm is monitored with a colorimeter and penicillin, such as penicillin G, is added to the medium at an initial stage of the logarithmic growth phase (OD:0.1 –0.4) in a concentration of 0.1 to 2.0 U/ml. Culturing is continued to an OD value of 0.3–0.5, and then cells are harvested and washed with the SSM medium. The washed cells are resuspended in a suitable hypertonic medium such as PFM medium (pH 7.0–8.5) wherein 0.4M sucrose and 0.01M MgCl$_2$.6H$_2$O are added to 2 fold diluted SSM medium, and RCG medium (pH 7.0–8.5) consisting of 5 g/l glucose, 5 g/l casein hydrolysate, 2.5 g/l yeast extract, 3.5 g/l K$_2$HPO$_4$, 1.5 g/l KH$_2$PO$_4$, 0.41 g/l MgCl$_2$.6H$_2$O, 10 mg/l FeSO$_4$. 7H$_2$O, 2 mg/l MnSO$_4$.(4–6)H$_2$O, 0.9 mg/l ZnSO$_4$.7H$_2$O, 0.4 mg/l CuSO$_4$.5H$_2$O, 0.09 mg/l Na$_2$B$_4$O$_7$.10H$_2$O, 0.04 mg/l (NH$_4$)$_6$Mo$_7$O$_{24}$. 4H$_2$O, 30 µg/l biotin, 2 mg/l thiamine hydrochloride and 135 g/l sodium succinate or RCGP medium which consists of RCG medium and 3% polyvinyl pyrrolidone. To the cell suspension, lysozyme is added to a final concentration of 0.2 to 10 mg/ml, and the mixture is allowed to react at a temperature of 30° to 37° C. Protoplast formation proceeds with time and is monitored with an optical microscope. The period required for the conversion of most cells to protoplasts depends on the concentrations of the penicillin used for the lysozyme-sensitization and the amount of lysozyme used. The period is 3–24 hours under the conditions mentioned above.

Since protoplasts formed are destroyed under hypotonic conditions, the extent of the formation of protoplast is determined indirectly from the number of normal cells surviving under hypotonic conditions. Generally, the ratio of surviving normal cells are kept below $10^{-4}$ per lysozyme-treated normal cell.

The protoplasts prepared as above have colonyforming (regenerating) ability on a suitable hypertonic agar medium. As a regeneration medium, a nutrient medium, a semi-synthetic medium or a synthetic medium containing various amino acids, which contains 0.3 to 0.8M sodium succinate and 0.5 to 6% polyvinyl pyrrolidone with a molecular weight of 10,000 or 40,000 is preferably used. Generally, a semi-synthetic medium, RCGP agar medium (pH 7.2) wherein 1.4% agar is added to the RCGP medium is used. Regeneration is carried out at a temperature of 25° to 35° C. The cultivation time required for the regeneration of protoplasts depends upon the strain used but usually in 10 to 14 days colonies can be picked up. The efficiency of the regeneration of protoplasts on the RCGP medium also depends on the strain used, the concentrations of the penicillin added during the cultivation and the concentration of lysozyme used. The efficiency is generally $10^{-2}$–$10^{-4}$ cells per normal cell treated with lysozyme.

2. Transformation of the protoplasts with a recombinant DNA:

Introduction of a recombinant DNA into the protoplast is carried out by mixing the protoplast and the DNA in a hypertonic solution which protects the protoplast and by adding to the mixture polyethyleneglycol (PEG, average molecular weight: 1,540–6,000) or polyvinylalcohol (PVA, degree of polymerization: 500–1,500) and a divalent metal cation which stimulates the uptake of DNA. As a stabilizing agent for the hypertonic conditions, those generally used to protect protoplasts of other microorganisms such as sucrose and sodium succinate are also employed. PEG and PVA can be used at a final concentration of 5 to 60% and 1 to 20%, respectively. Divalent metal cations such as $Ca^{++}$, $Mg^{++}$, $Mn^{++}$, $Ba^{++}$ and $Sr^{++}$ are effectively used alone or in combination at a final concentration of 1 to 100 mM. Transformation is carried out satisfactorily at 0° to 25° C.

3. Regeneration of the protoplasts to normal cells and selection of a transformant:

Regeneration of the protoplast transformed with a recombinant DNA is carried out in the same way as mentioned above by spreading the protoplast on a hypertonic agar medium such as RCGP medium containing sodium succinate and olyvinyl pyrrolidone and incubating at a temperature wherein normal cells can grow, generally 25° to 35° C. Transformants are obtained by selecting for the phenotype derived from donor DNAs. The selection may be carried out simultaneously with regeneration on a hypertonic agar medium or may be carried out on a hypotonic agar medium after non-selective reversion to normal cells on a hypertonic agar medium.

In the case of the lysozyme-sensitive strains described as the preferred host microorganisms for cloning, the transformation may be carried out by the steps described in (1) to (3) except that the cultured cells are directly treated with lysozyme without prior treatment with penicillin. In that case, transformants are obtained at an efficiency of $10^{-3}$ to $10^{-4}$ per regenerated cell.

The phenotypic expression of the recombinant DNA is carried out by growing the transformant in a conventional nutrient medium. Appropriate reagents may be added to the medium according to the phenotypes expected from the genes on the recombinant DNA.

The thus obtained transformant is cultured in a conventional manner used in the production of phenylalanine by fermentation. That is, the transformant is cultured in a conventional medium containing carbon sources, nitrogen sources, inorganic materials, amino acids, vitamines, etc. under aerobic conditions, with adjustment of temperature and pH. Phenylalanine, thus accumulated in the medium, is recovered.

As the carbon source, various carbohydrates such as glucose, glycerol, fructose, sucrose, maltose, mannose, starch, starch hydrolyzate and molasses, polyalcohols and various organic acids such as pyruvic acid, fumaric acid, lactic acid and acetic acid may be used. According to the assimilability of the microorganism strain used, hydrocarbon and alcohols are employed. Blackstrap molasses is most preferably used.

As the nitrogen source, ammonia, various inorganic or organic ammonium salts such as ammonium chloride, ammonium sulfate, ammonium carbonate and ammonium acetate, urea, and nitrogenous organic substances such as peptone, NZ-amine, meat extract, yeast extract, corn steep liquor, casein hydrolyzate, fish meal or its digested product, defatted soybean or its digested product and chrysalis hydrolyzate are appropriate.

As the inorganic materials, potassium dihydrogenphostate, dipotassium hydrogenphosphate, ammonium sulfate, ammonium chloride, magnesium sulfate, sodium chloride, ferrous sulfate, manganese sulfate and calcium carbonate may be used. Vitamines and amino acids required for the growth of microorganisms may not be added, provided that they are supplied with other components mentioned above.

Culturing is carried out under aerobic conditions with shaking or aeration-agitation. Culturing temperature is preferably 20° to 40° C. The pH of the medium during culturing is maintained around neutral. Culturing is continued until a considerable amount of phenylalanine is accumulated, generally for 1 to 5 days.

After completion of the culturing, cells are removed and phenylalanine is recovered from the culture liquor by conventional manners such as treatment with active carbon or ion exchange resin.

Certain specific embodiments of the present invention are illustrated by the following representative examples reflecting actual experimental data.

EXAMPLE 1

Cloning of a gene coding for chorismate mutase and prephenate dehydratase derived from *Corynebacterium glutamicum* K38 strain and production of L-phenylalanine by the expression of the gene in *Corynebacterium glutamicum*:

(1) Preparation of the chromosomal DNA and plasmid pCG11:

The chromosomal DNA of *Corynebacterium glutamicum* K38 FERM P-7087 (FERM BP-454) was prepared by the following method:

A seed culture in NB medium was inoculated into 400 ml of SSM. Culturing was carried out with shaking at 30° C. The optical density (OD) at 660 nm was monitored with a Tokyo Koden colorimeter and penicillin G was added at an OD value of 0.2 to a concentration of 0.5 unit/ml. Culturing was continued to an OD value of about 0.6.

Cells were harvested from the culture broth and washed with TES buffer (pH 8.0) consisting of 0.03M tris(hydroxymethyl) aminomethane-HCl (referred to as Tris hereinafter), 0.005M EDTA and 0.05M NaCl. The cells were suspended in a lysozyme solution (pH 8.0) consisting of 12.5% sucrose, 0.1M NaCl, 0.05M Tris and 0.8 mg/ml lysozyme to make 10 ml of a suspension which was allowed to react at 37° C. for 4 hours. High molecular chromosomal DNAs were isolated from the cells by the method of Saito et al., Biochim. Biophys. Acta, 72, 619 (1963).

Separately pCG11 used as a vector was prepared from the cultured cells of Corynebacterium glutamicum L-22 strain harboring pCG11 by the following method.

The strain was grown with shaking at 30° C. in 400 ml of NB medium (pH 7.2) to an OD value of about 0.7. Cells were harvested and washed with TES buffer. The cells were suspended in 10 ml of the aforementioned lysozyme solution and allowed to react at 37° C. for 2 hours. Then 2.4 ml of 5M NaCl, 0.6 ml of 0.5M EDTA (pH 8.5) and 4.4 ml of a solution consisting of 4% sodium lauryl sulfate and 0.7M NaCl were added successively. The mixture was stirred slowly and allowed to stand on an ice water bath for 15 hours. The whole lysate was centrifuged at 4° C. under 69,400 ×g for 60 minutes. The supernatant fluid was recovered and 10% (by weight) polyethyleneglycol (PEG) 6,000 (product of Nakarai Kagaku Yakuhin Co.) was added. The mixture was stirred slowly to dissolve completely and then kept on an ice water bath. After 10 hours, the mixture was subjected to centrifugation at 1,500 ×g for 10 minutes to recover a pellet. The pellet was redissolved gently in 5 ml of TES buffer and 2.0 ml of 1.5 mg/ml ethidium bromide was added. Then, cesium chloride was added to adjust the density of the mixture to 1.580. The solution was centrifuged at 18° C. at 105,000 ×g for 48 hours. After the density gradient centrifugation, a convalently-closed circular DNA was detected under UV irradiation as a high density band located in the lower part of the centrifugation tube. The band was taken out from the side of the tube with an injector to obtain a fraction containing pCG11 DNA. To remove ethidium bromide, the fraction was treated five times with an equal amount of cesium chloride saturated isopropyl alcohol solution consisting of 90% by volume isopropyl alcohol and 10% TES buffer solution. Then, the residue was dialysed against TES buffer solution.

(2) Cloning of the gene responsible for the phenotype resistant to para-fluorophenylalanine (PFP):

In this step, 5 units of restriction enzyme BglII (product of Takara Shuzo Co.) was added to 100 μl of a BglII reaction solution (pH 7.5) consisting of 10 mM Tris, 7 mM MgCl$_2$, 60 mM NaCl and 7 mM 2-mercaptoethanol and containing 3 μg of pCG11 plasmid DNA and 5 units of BamHI (product of Takara Shuzo Co.) was added to 100 μl of restriction enzyme BamHI reaction solution (pH 8.0) consisting of 10 mM Tris, 7 mM MgCl$_2$, 100 mM NaCl, 2 mM mercaptoethanol and 0.01% bovine serum albumin and containing 9 μg of the chromosomal DNA. The mixture was allowed to react at 37° C. for 60 minutes and heated at 65° C. for 10 minutes to stop the reaction. 40 μl of a T4 ligase buffer solution (pH 7.6) consisting of 660 mM Tris, 66 mM MgCl$_2$ and 100 mM dithiothreitol, 40 μl of 5 mM ATP, 0.4 μl of T4 ligase (product of Takara Shuzo Co., 1 unit/μl) and 120 μl of H$_2$O were added. The mixture was allowed to react at 12° C. for 16 hours.

(3) Transformation with recombinant plasmids:

The above ligation mixture was provided for the following transformation. As the recipient for the transformation, *Corynebacterium glutamicum* L-15 ATCC 31834 was used.

The seed culture of L-15 strain was inoculated into NB medium and culturing was carried out with shaking at 30° C. Cells were harvested at an OD value of 0.6. The cells were suspended at about $10^9$ cells/ml in RCGP medium (pH 7.6) [consisting of 5 g/l glucose, 5 g/l casamino acid, 2.5 g/l yeast extract, 3.5 g/l K$_2$HPO$_4$, 1.5 g/l KH$_2$PO$_4$, 0.41 g/l MgCl$_2$.6H$_2$O, 10 mg/l FeSO$_4$.7H$_2$O$_4$. 7H$_2$O, 2 mg/l MnSO$_4$.(4–6) H$_2$O, 0.9 mg/l ZnSO$_4$.7H$_2$O, 0.04 mg/l (NH$_4$)$_6$Mo$_7$O$_{24}$.4-H$_2$O, 30 μg/l biotin, 2 mg/l thiamine hydrochloride, 135 g/l sodium succinate and 30 g/l polyvinyl pyrrolidone with a molecular weight of 10,000]containing 1 mg/ml lysozyme. The suspension was put in an L-tube and stirred slowly at 30° C. for 5 hours to obtain protoplasts.

Then, 0.5 ml of the protoplast suspension was put in a small test tube and centrifuged at 2,500 ×g for 5 minutes. The protoplasts were resuspended in 1 ml of TSMC buffer (pH 7.5) consisting of 10 mM magnesium chloride, 30 mM calcium chloride, 50 mM Tris and 400 mM sucrose and again subjected to centrifugation and washing. The washed protoplasts were resuspended in 0.1 ml of TSMC buffer solution. 100 μl of a mixture (1:1 by volume) of a two-fold concentrated TSMC buffer and the ligated DNA mixture described above was added to the protoplast suspension. Then, 0.8 ml of a solution containing 20% PEG 6,000 in TSMC buffer solution was added to the mixture. After 3 minutes, 2 ml of RCGP medium (pH 7.2) was added and the mixture was centrifuged at 2,500×g for five minutes. The supernatant fluid was removed and the protoplasts were suspended in 1 ml of RCGP medium. Then, 0.2 ml of the suspension was spread on RCGP agar medium (pH 7.2) containing 200 μg/ml spectinomycin and 1.4% agar and incubated at 30° C. for 7 days.

All the colonies formed on the agar medium were scraped, washed with physiological saline solution and centrifuged two times. The cells were spread on a minimal agar medium M1 (pH 7.2) consisting of 10 g/l glucose, 1 g/l NH$_4$H$_2$PO$_4$, 0.2 g/l KCl, 0.2 g/l MgSO$_4$.7-H$_2$O, 10 mg/l FeSO$_4$. 7H$_2$O, 0.2 mg/l MnSO$_4$.(4–6)-H$_2$O, 0.9 mg/l ZnSO$_4$.7H$_2$O, 0.4 mg/l CuSO$_4$.5H$_2$O, 0.09 mg/l Na$_2$B$_4$O$_7$.10H$_2$O, 0.04 mg/l (NH$_4$)$_6$Mo$_7$O$_{24}$.4H$_2$O, 50 μg/l biotin, 2.5 mg/l p-aminobenzoic acid, 1 mg/l thiamine hydrochloride and 16 g/l agar and containing 100 μg/ml spectinomycin and 0.5 mg/ml PFP and incubated at 30° C. for 2 days. The transformants which are resistant to spectinomycin and PFP were obtained from the colonies formed.

A plasmid DNA was isolated from cells of one of the transformants by the same ethidium bromide-cesium chloride density gradient centrifugation method as in step (1) above and designated pCS-CM1.

Furthermore, the same ligation mixture was used to transform a Corynebacterium glutamicum strain requiring phenylalanine and tyrosine for its growth (defective in chorismate mutase and prephenate dehydratase) by the same method described above. The selection of spectinomycin-resistant transformant on M1 agar medium yielded prototrophic clones, which required neither phenylalanine nor tyrosine for its growth. Plasmid DNAs were isolated from these transformants as mentioned above. A plasmid pCS-CM2 obtained from one of the transformants was digested with restriction endonucleases and analysed by agarose gel electrophoresis. The analysis showed that a BamHI DNA fragment of about 9.4 Kb was inserted into a unique BglII cleavage site of pCG11 in pCS-CM2.

Further, digestions with other restriction endonucleases such as EcoRI, SalI, HindIII, and the like gave the same cleavage patterns in pCS-CM1 and pCS-CM2, indicating that both plasmids have the same physical structure as shown below.

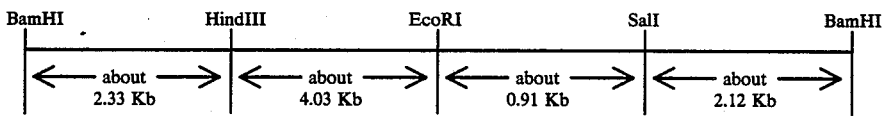

When a phenylalanine- and tyrosine-requiring *Corynebacterium glutamicum* strain was transformed with pCS-CM1 and pCS-CM2 to select for spectinomycin resistance, the resulting transformants all exhibited prototrophy and resistance to PFP, and carried the same plasmids as pCS-CM1 and pCS-CM2.

These results indicate that the BamHI DNA fragment of about 9.4Kb cloned in pCS-CM1 and pCS-CM2 contains the genes encoding for chorysmate mutase and prephenate dehydratase of *Corynebacterium glutamicum* K38 and the DNA fragment can confer resistance to PFP on the host microorganism.

(4) Production of phenylalanine by the transformant:

*Corynebacterium glutamicum* K38 (FERM P-7087, FERM BP-454) which produces phenylalanine was transformed with pCS-CM2 as mentioned above. The thus obtained transformant has been deposited with the Fermentation Research Institute as *Corynebacterium glutamicum* K39, FERM P-7088 (FERM BP-459).

*Corynebacterium glutamicum* K39 and its pCS-CM2-carrying strain were tested for L-phenylalanine production as follows.

The strain was cultured in NB medium at 30° C. for 16 hours and 0.5 ml of the culture liquor was inoculated in 5 ml of a production medium P4 adjusted to pH 7.2 consisting of 100 g/l molasses, 20 g/l $(NH_4)_2SO_4$, 0.5 g/l $KH_2PO_4$, 0.5 g/l $K_2HPO_4$, 0.25 g/l $MgSO_4 \cdot 7H_2O$, and 20 g/l $CaCO_3$. Culturing was carried out at 30° C. for 96 hours. The culture filtrate was subjected to paper chromatography, color reaction with ninhydrin and the amount of L-phenylalanine formed was determined colorimetrically. The results are shown in Table 1.

TABLE 1

| Strain | Amount of L-phenylalanine (mg/ml) |
|---|---|
| *Corynebacterium glutamicum* K38 | 6.0 |
| *Corynebacterium glutamicum* K39 | 9.6 |

What is claimed is:

1. A process for producing phenylalanine which comprises transforming a host microorganism belonging to the genus *Corynebacterium* or *Brevibacterium* with a recombinant DNA comprising a DNA fragment containing a gene coding for at least one of chorismate mutase and prephenate dehydratase obtained from a microorganism belonging to the genus *Corynebacterium* or *Brevibacterium*, culturing the transformant in a nutrient medium containing a molasses carbon source, accumulating phenylalanine in the culture medium and recovering phenylalanine therefrom.

2. The process according to claim 1, wherein the host microorganism is a microorganism of the species *Corynebacterium glutamicum*, *Corynebacterium herculis*, *Brevibacterium flavum* or *Brevibacterium lactofermentum*.

3. An isolated DNA fragment or a recombinant DNA containing the DNA fragment, which DNA fragment or recombinant DNA contains a gene coding for at least one of chorismate mutase and prephenate dehydratase obtained from a microorganism belonging to the genus *Corynebacterium* or *Brevibacterium*.

4. A microorganism belonging to the genus *Corynebacterium* or *Brevibacterium* and having a native ability to produce phenylalanine, said microorganism containing a recombinant DNA comprising a DNA fragment containing a gene coding for at least one of chorismate mutase and prephenate dehydratase, said gene obtained from a microorganism belonging to the genus *Corynebacterium* or *Brevibacterium*.

5. *Corynebacterium glutamicum* K39, FERM P-7088 (FERM BP-459).

* * * * *

UNITED STATES PATENT AND TRADEMARK OFFICE
CERTIFICATE OF CORRECTION

PATENT NO. : 4,908,312
DATED : March 13, 1990
INVENTOR(S) : AKIO OZAKI ET AL.

Page 1 of 2

It is certified that error appears in the above-identified patent and that said Letters Patent is hereby corrected as shown below:

ON TITLE PAGE:

AT [54] TITLE

"PHENYLANANINE" should read --PHENYLALANINE--.

AT [56] REFERENCES CITED

Other Publications, "pl" should be deleted and "Archnes" should read --Archives-- and "Goiorishankar, J.," should read --Gowishankar, J.,--.

COLUMN 1

Line 2, "PHENYLANANINE" should read --PHENYLALANINE--.
Line 68, "phenylalahine" should read --phenylalanine--.

COLUMN 4

Line 48, "0.04 mg/l $(NH_4)_6Mo_7O_{24}4H_2O$, 30 µg" should read --0.04 mg/l $(NH_4)_6Mo_7O_{24} \cdot 4H_2O$, 30 µg/l--.

COLUMN 5

Line 62, "olyvinyl pyrrolidone" should read --polyvinyl pyrrolidone--.

COLUMN 6

Line 9, "$10^{-3}$" should read --$10^{-2}$--.

UNITED STATES PATENT AND TRADEMARK OFFICE
CERTIFICATE OF CORRECTION

PATENT NO. : 4,908,312
DATED : March 13, 1990
INVENTOR(S) : AKIO OZAKI ET AL.

It is certified that error appears in the above-identified patent and that said Letters Patent is hereby corrected as shown below:

COLUMN 8

Line 22, "mg/l $FeSO_4 \cdot 7H_2O_4 \cdot 7H_2O$," should read --mg/l $FeSO_4 \cdot 7H_2O$,--.

Signed and Sealed this

Thirteenth Day of August, 1991

*Attest:*

*Attesting Officer*

HARRY F. MANBECK, JR.

*Commissioner of Patents and Trademarks*